United States Patent [19]

Keyes, IV et al.

[11] Patent Number: 5,025,665
[45] Date of Patent: Jun. 25, 1991

[54] NON-CONTACTING ON-LINE PAPER STRENGTH MEASURING SYSTEM

[75] Inventors: Marion A. Keyes, IV, Chagrin Falls; William L. Thompson, Montville, both of Ohio

[73] Assignee: Elsag International B.V., Amsterdam, Netherlands

[21] Appl. No.: 359,536

[22] Filed: Jun. 1, 1989

[51] Int. Cl.⁵ ........................ G01N 29/18; G01H 5/00
[52] U.S. Cl. ......................................... 73/597; 73/602; 73/159
[58] Field of Search ................. 73/655, 597, 598, 643, 73/159, 602

[56] References Cited

U.S. PATENT DOCUMENTS

| | | | |
|---|---|---|---|
| 3,952,583 | 4/1976 | Rosati | 73/655 |
| 4,291,577 | 9/1981 | Baum et al. | 73/597 |
| 4,622,853 | 11/1986 | Leugers | 73/597 |
| 4,674,332 | 6/1987 | Pace et al. | 73/597 |
| 4,833,928 | 5/1989 | Luukkala et al. | 73/655 |

Primary Examiner—Hezron E. Williams
Assistant Examiner—Rose M. Finley
Attorney, Agent, or Firm—Vytas R. Matas; Robert J. Edwards; Daniel S. Kalka

[57] ABSTRACT

An on-line system that measures the strength of material within a web without contacting same is disclosed. Two laser sources having beams which impinge upon the web of material are positioned so that their respective beams are spaced a predetermined distance apart. The first laser source induces a radially propagating ultrasonic wave within the material. The ultrasonic wave causes the beam from the second laser source to be reflected and intercepted by a light sensor permitting the velocity of the wave and the strength of the material to be determined.

8 Claims, 2 Drawing Sheets

NON-CONTACTING ON-LINE PAPER STRENGTH MEASURING SYSTEM

TECHNICAL FIELD

The present invention relates generally to a system for measuring the strength of material within a web and, more particularly, to an on-line system that measures the strength of paper in a web without contacting same.

BACKGROUND ART

A major quality consideration for the production of sheet materials, such as paper, is strength. Until recently, all strength measurements with respect to such sheet materials were made by off-line laboratory measurements. Recently, on-line measurements have been introduced using contacting gauging techniques that rely on the relationship between Young's Modulus and the speed of sound according to the following equation:

$$Y = K_1 s^2$$

Where $k_1$ is a function of the density of the material and s is the speed of sound within the material.

The methods of Baum and Habeger, as set forth in U.S. Pat. No. 4,291,577, and others, rely on rotating wheels which contact the moving web of paper or other material whose strength is being measured. The wheels contain piezoelectric or magnetostrictive transducers in their outer peripheries to create a localized contraction and expansion in the moving web of material. This contraction and expansion creates a sonic wave that travels radially from the spot of creation. Measuring the speed of sound within the material, which is the reciprocal of the transit time between two points of known separation, is used in conjunction with the density of the material to provide a measurement of the strength of the material. This approach has some inherent disadvantages among which are that the required commutation and mechanical contact produce a signal that contains a significant amount of noise, the rotating wheels are prone to fail, mechanical structures are inevitably more costly and have more parts than electronic devices, the direct contact of the wheels with the material limits the measurement of strength to a single direction (either across the web or along the web), and mechanical methods with slippage and commutation are inherently less accurate than non-mechanical methods.

Photoacoustic interaction has been used to induce ultrasonic waves into a continuous, fast moving web of paper. U.S. Pat. No. 4,674,332 (Pace, et al) discloses the use of a nitrogen laser to illuminate paper with high power ultraviolet pulses. A portion of this optical energy is converted into heat creating an acoustic wave from the resulting thermal expansion. A contacting, ultrasonic sensor or a microphone positioned on the opposite side of the paper receives the acoustic wave and provides an indication of the speed of sound through the paper which can be utilized to determine the strength of the paper in its direction of movement.

Another application of a laser to generate acoustic waves in paper is provided in U.S. Pat. No. 4,622,853 (Leugers). The apparatus disclosed in this reference utilizes a Neodymium/Yttrium-Aluminum-Garnet (Nd/YAG) laser with a frequency doubler to illuminate a spot on a moving web of paper. The ultrasonic wave in the paper is detected by an ultrasonic transducer in contact with the paper.

Because of the disadvantages that are inherent in a measuring system that requires contact with the material whose strength is being measured, it has become desirable to develop an on-line, measuring system that does not require such contact.

SUMMARY OF THE INVENTION

The present invention solves the problems associated with the prior art and other problems by providing an on-line system that measures the strength of material within a web without contacting same. The foregoing is accomplished by utilizing two spaced-apart laser sources having beams which intercept the web of material whose strength being measured. The distance between the points of impingement of the beams from the laser sources is known. The first laser source generates localized spot heating which creates thermal expansion in the web of material. This thermal expansion creates an ultrasonic wave which propagates through the web in a radial direction. The wave causes the beam from the second laser source to be reflected by the material and the reflected beam is intercepted by a light sensor. By calculating the elapsed time between the transmission of the first beam into the material and the receipt of the second beam by the light source, the velocity of the ultrasonic wave within the material can be determined. The velocity of the ultrasonic wave is then combined with a measurement of the density of the material to determine the strength of the material.

DESCRIPTION OF THE PREFERRED EMBODIMENT

Figure 1:
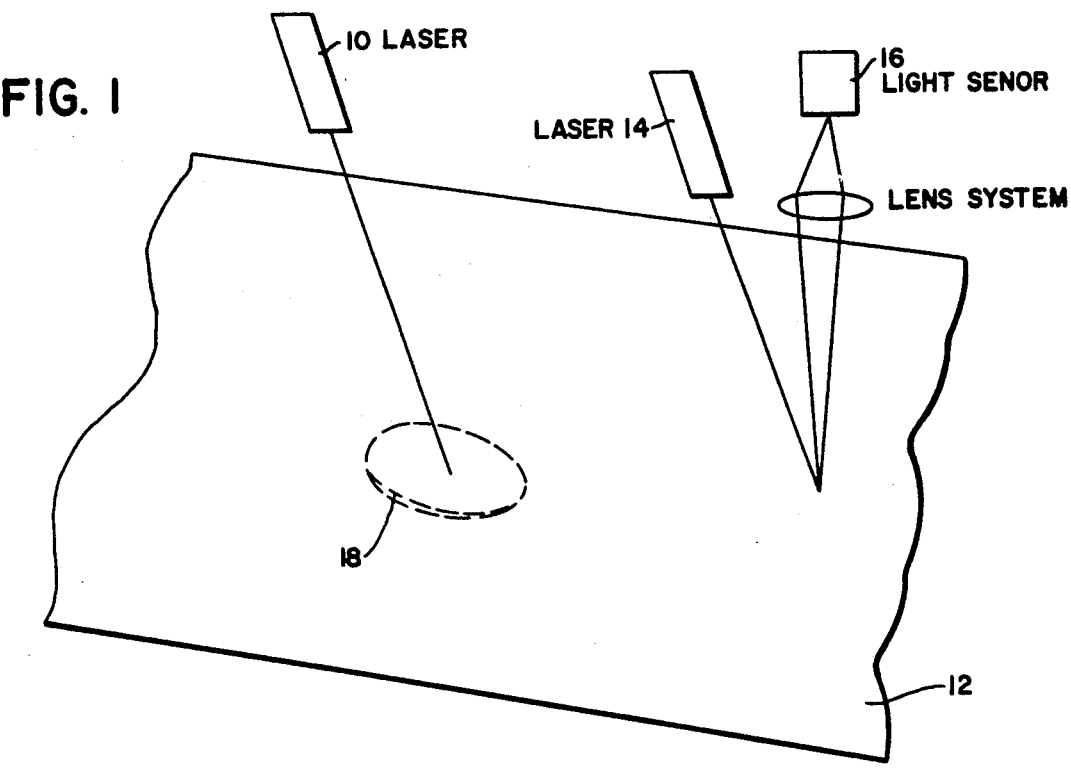
FIG. 1 is a schematic diagram of the measuring system of the present invention.

Referring now to the drawings where the illustrations are for the purpose of describing the preferred embodiment of the present invention and are not intended to limit the invention hereto, FIG. 1 is a schematic diagram of the measuring system of the present invention. The measuring system includes a first laser source 10 directed toward a web 12 of material whose strength is to be measured, a second laser source 14 similarly directed toward the web 12 of material and a light sensor 16 located adjacent second laser source 14 and positioned so that its focal point is coincident with the point of impingement of the beam from second laser source 14 on the web 12 of material. The distance "d" between the points of impingement of the beams from laser sources 10 and 14 on web 12 of material is known.

The present invention utilizes an ultrasonic wave pattern induced into the moving web 12 of material by pulses produced by first laser source 10 which generates localized spot heating. Such localized spot heating creates thermal expansion in the material whose strength is being measured. This expansion perturbation creates a wave which propagates through the web 12 of material in a radial direction giving an elliptical wave front, shown generally by the numeral 18, due to the anisotropy in the wave velocity with the direction of web movement. Measurement of wave velocity in a particular direction can be utilized to determine the strength of the material in that direction.

The light sensor 16 measures the foregoing wave front by viewing the crests and valleys of the ultrasonic wave as it passes thereunder. Separate viewing laser and light detection systems may be used for the cross-travel direction and the width-travel direction or a single system may be scanned to read both directions. The time of arrival of the sensed pulse is compared with the time of impingement of the beam from first laser source 10 into the web 12 of material, and the difference in time is utilized to calculate the speed of sound within the material. The foregoing speed of sound is then used in conjunction with the density of the material to determine the strength of the material being tested. The foregoing system operates at the speed of light and, as such, any time delays are inconsequential.

First laser source 10 is a $CO_2$ laser having an output power of approximately 5.5 watts and is typically pulsed at a rate of 10 pulses per second producing a pulse having a width of approximately 100 $\mu$sec. or shorter. Second laser source 14 is a HeNe laser having an output power of approximately 2 milliwatts which is operated continuously. Light sensor 16 can be a silicon photo-detector producing an output in millivolt range.

Figure 2:
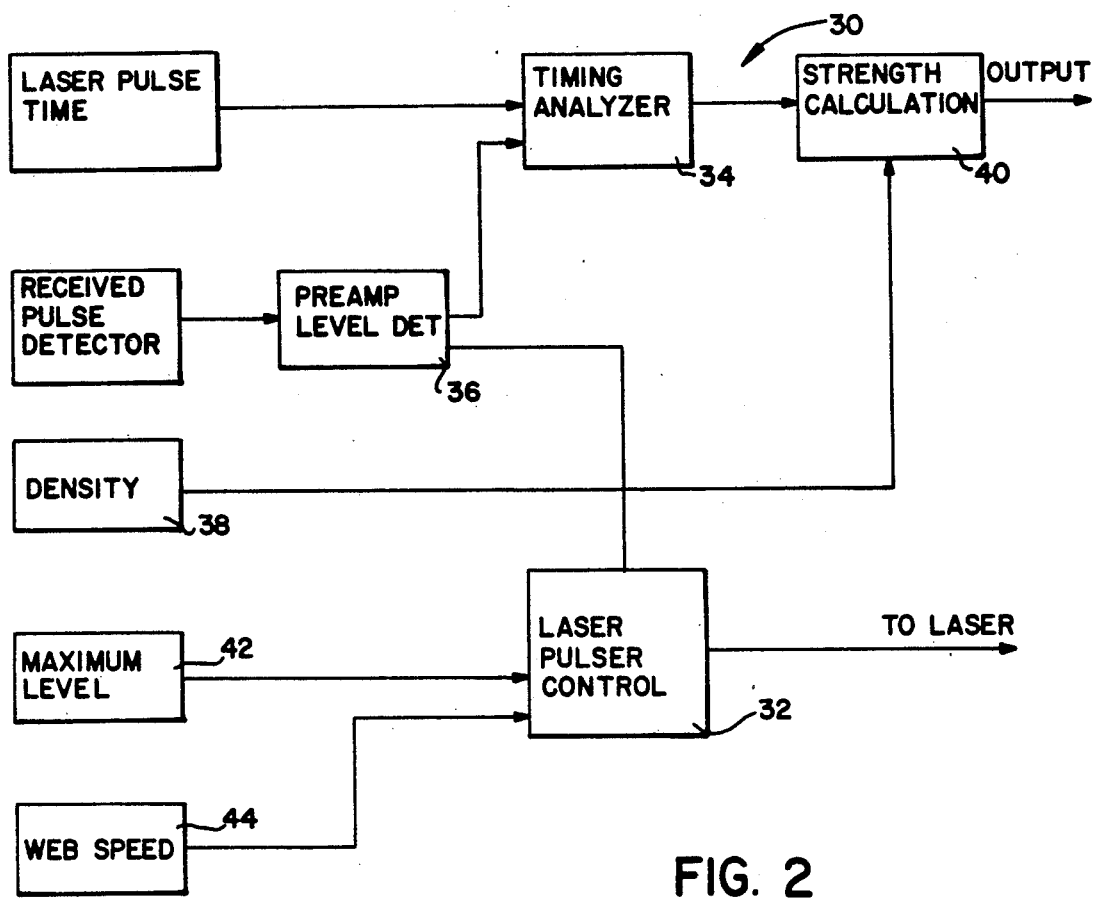
FIG. 2 is a schematic diagram of the control circuit utilized by the measuring system shown in FIG. 1.

Referring now to FIG. 2, a schematic diagram of the control circuit 30 associated with the present invention is illustrated. This control circuit 30 includes a laser pulser control 32 which regulates the operation of first laser source 10. Each time the first laser source 10 is pulsed, a first timing pulse is transmitted by the laser pulser control 32 to a timing analyzer 34. After the resulting ultrasonic wave caused by the pulse produced by first laser source 10 has propagated through the material whose strength is being measured, the light sensor 16 intercepts the light emanating from second laser source 14 and reflected by the material, and transmits a pulse to a preamp level detector 36 which, in turn, transmits a second timing pulse to timing analyzer 34. An output of the preamp level detector 36 is connected to an input to the laser pulser control 32 and causes the pulser control 32 to increase or decrease the magnitude of the pulses produced by first laser source 10 so that the ultrasonic pulses detected by light sensor 16 will be of sufficient magnitude for detection purposes. The timing analyzer 34 determines the elapsed time, $\Delta t$, between the transmission of the first timing pulse by the laser pulser control 32 and the receipt of the second timing pulse from the preamp level detector 36. The foregoing elapsed time $\Delta t$ and the known distance d between points of impingement on the web 12 of the beams emanating from laser sources 10 and 14 are then combined with a measurement of material density provided by a density measuring device 38 in a strength calculation device 40 to determine the velocity v of the ultrasonic wave within the material whose strength is being measured. An appropriate density measuring device 38 is disclosed in U.S. Pat. No. 3,586,601 entitled "Basis Weight Control System for a Paper Making Machine". The strength calculating device 40, which can be a microprocessor, determines the strength of the material since material strength is proportional to $K_1 v^2$ where V is the speed of sound in the material.

A maximum laser level control 42 and a web speed control 44 are provided as inputs to the laser pulser control 32. The maximum laser level control 42 ensures that first laser source 10 causes no damage to the material whose strength is being measured and the web speed signal 44 allows the laser level to increase as the web speed increases.

Figure 3:
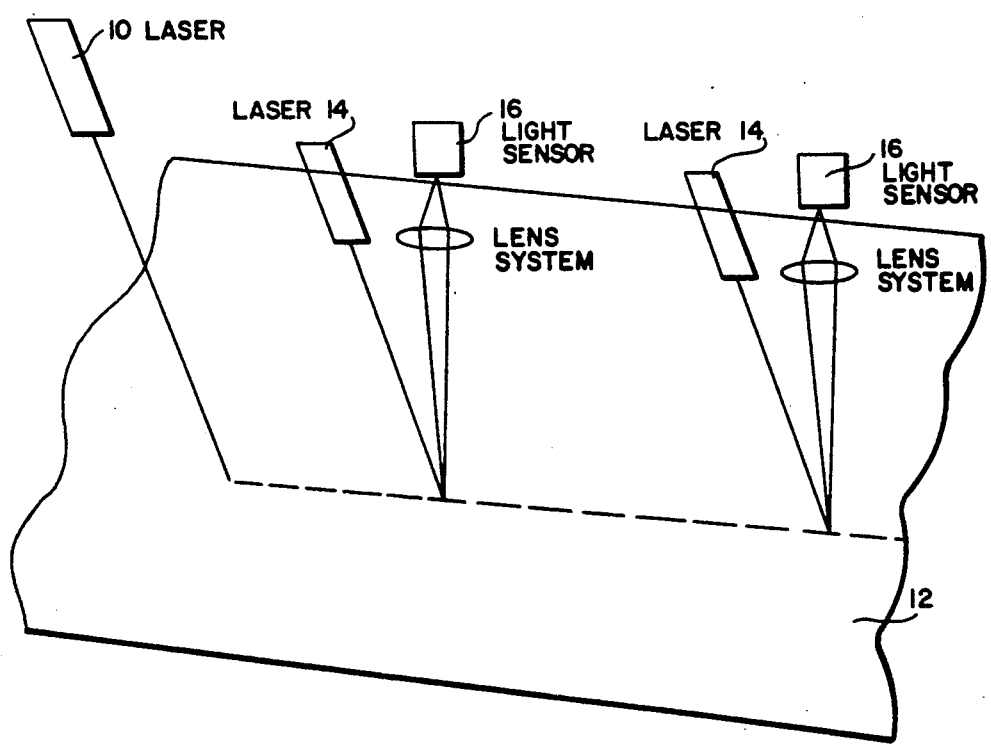
FIG. 3 is a schematic diagram of an alternate embodiment of the measuring system of the present invention utilizing two light sensors.

An alternate embodiment of the present invention is shown in FIG. 3. In this Figure, two sensing arrangements are employed. Inasmuch as the elements are the same as those shown in FIG. 1 and carry the same reference numerals, further discussion of same will not be undertaken. The main advantage of this embodiment is that the use of two sensing arrangements permits the correlation of the received wave shapes using digital correlation or digital signal processing techniques so as to improve the accuracy of the resulting strength measurement and to allow for less precision and repeatability in the shape of the generated ultrasonic wave shape.

Figure 4:
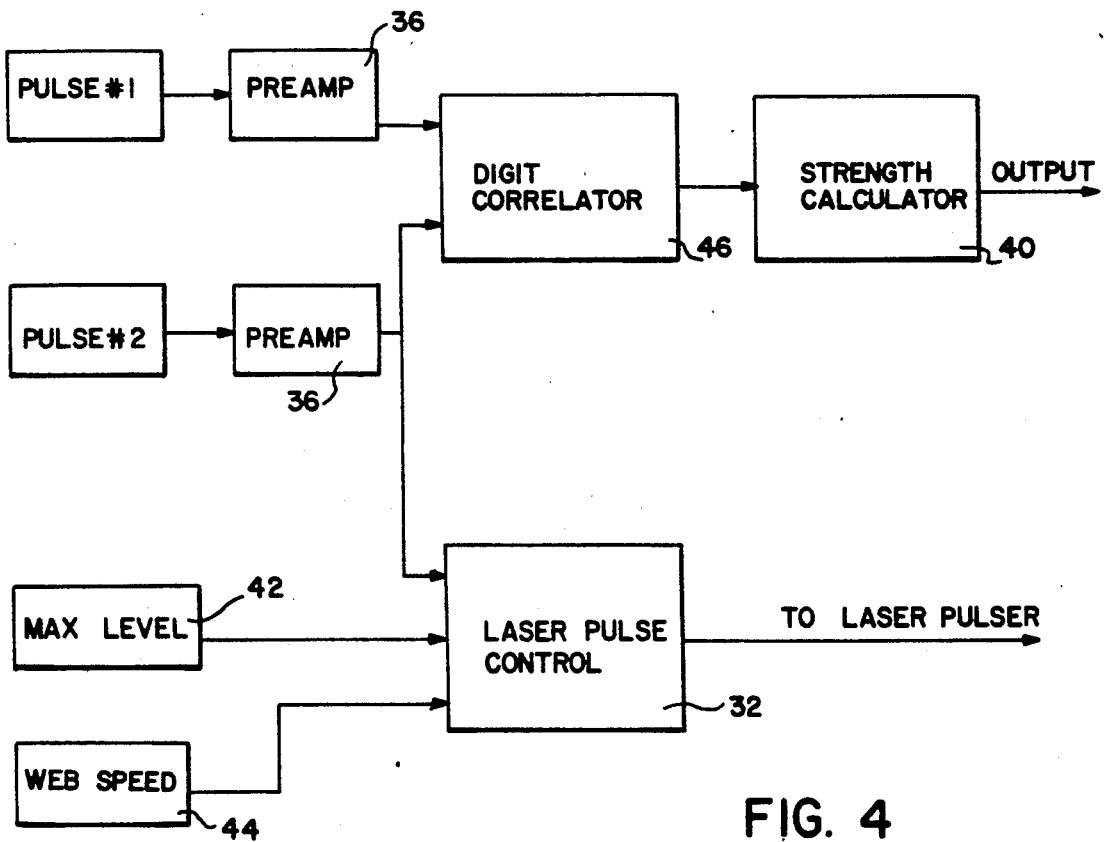
FIG. 4 is a schematic diagram of the control circuit utilized by the embodiment of the invention shown in FIG. 3.

FIG. 4 illustrates the control circuit utilized by the embodiment of the invention illustrated in FIG. 3. Here again, those elements which are similar to the elements shown in FIG. 2 carry the same reference numerals and will not be discussed. The primary difference between the schematic diagram shown in FIG. 4 and that shown in FIG. 2 is the use of a digital correlator 46 which, as previously indicated, correlates the wave shapes received by the light sensors 16 and utilizes digital correlation or digital signaling processing techniques to determine the time required for the ultrasonic wave shape to traverse the web of material. Since two light sensors are utilized in the embodiment shown in FIG. 3 and FIG. 4, it is possible to use less precise and less expensive pulse sources to induce the waves in the moving web of material.

Regardless of the embodiment of the invention utilized, the present invention provides the following advantages:

1) The measuring system is on-line and does not contact the web of material;

2) The system has omnidirectional measurement capability;

3) Material strength can be determined across the entire web of material;

4) The system is adaptable to rough or hot material surfaces;

5) The system can utilize digital signal processing techniques; and

6) Power levels are variable in order to optimize operation of the system without causing damage to the web of material.

Certain modifications and improvements will occur to those skilled in the art upon reading the foregoing. It should be understood that all such modifications and improvements have been deleted herein for the sake of conciseness and readability, but are properly within the scope of the following claims.

We claim:

1. A system for measuring the strength of a material within a web without contacting same, comprising:
   a first source of light beams positioned such that said light beams contact the material and induce an ultrasonic wave therein;
   at least one second source of light beams directed so as to illuminate said ultrasonic wave as it traverses past;
   light sensing means for detecting light reflected from the material as said ultrasonic wave traverses therethrough, said light sensing means being positioned at a predetermined distance from the point of inducement of said ultrasonic wave within the material, said at least one second source of light beams being positioned adjacent said light sensing means;

means for determining the velocity of said ultrasonic wave within the material, said determining means calculating velocity from elapsed time between transmission of the first light beam into the material and the detection of the at least one second light beam by said light sensing means;

means for determining the density of the material;

means for determining the strength of the material based on the velocity of said ultrasonic wave within the material and the density of the material; and means for varying the output of said first source of light beams.

2. The system as defined in claim 1 wherein said first light beam source is a laser having a pulsed output.

3. The system as defined in claim 1 wherein said at least one second light beam source is a laser having a continuous output.

4. A system for measuring the strength of a material within a web without contacting same, comprising:

a first source of light beams positioned such that said light beams contact the material and induce an ultrasonic wave therein;

at least one second source of light beams directed so as to illuminate said ultrasonic wave as it traverses past;

light sensing means for detecting light reflected from the material as said ultrasonic wave traverses therethrough, said light sensing means being positioned at a predetermined distance from the point of inducement of said ultrasonic wave within the material, said at least one second source of light beams positioned adjacent said light sensing means;

pulser control means for pulsing said first source of light beams and establishing a signal indicative thereof;

timing means in communication with said pulser control means and light sensing means for determining elapsed time between transmission of the first pulse of light beam and detection of the reflected at least one second light beam;

means for determining the velocity of said ultrasonic wave within the material, said determining means calculating velocity from the elapsed time from said timing means and the predetermined distance;

means for determining the density of the material;

means for determining the strength of the material based on the velocity of said ultrasonic wave within the material and the density of the material; and preamp level detecting means in communication with said light sensing means for transmitting a second timing pulse to said timing means which determines the elapsed time, said preamp level detecting means further being connected to said pulser control means for regulating magnitude of the pulses produced by said first source of light beams.

5. The system as defined in claim 4, wherein said first light beam source is a laser.

6. The system as defined in claim 4, wherein said at least one second light beam source is a laser having a continuous output.

7. The system as defined in claim 4, wherein said timing means includes a digital correlator for correlating wave shapes and digital correlations to determine elapsed time.

8. The system as defined in claim 7, wherein said light sensing means includes at least two light sensors positioned adjacent to at least two second sources of light beams.

* * * * *